United States Patent
Goldman et al.

(10) Patent No.: US 8,477,035 B2
(45) Date of Patent: Jul. 2, 2013

(54) SECURITY SYSTEM TRIGGERED BY HEART RATE DETECTION

(75) Inventors: Stuart O. Goldman, Scottsdale, AZ (US); Richard E. Krock, Naperville, IL (US); Karl F. Rauscher, Emmaus, PA (US); James P. Runyon, Wheaton, IL (US)

(73) Assignee: Alcatel Lucent, Paris (FR)

( * ) Notice: Subject to any disclaimer, the term of this patent is extended or adjusted under 35 U.S.C. 154(b) by 710 days.

(21) Appl. No.: 11/680,560

(22) Filed: Feb. 28, 2007

(65) Prior Publication Data

US 2008/0204558 A1 Aug. 28, 2008

(51) Int. Cl.
*G08B 23/00* (2006.01)
*G08B 5/22* (2006.01)
*A61B 5/00* (2006.01)
*H04M 11/04* (2006.01)
*H04M 11/00* (2006.01)

(52) U.S. Cl.
USPC .......... 340/573.1; 340/6.1; 340/7.5; 600/324; 455/404.2; 455/408

(58) Field of Classification Search
USPC ......... 340/573.1, 573.4, 575, 539.16, 870.09; 600/300
See application file for complete search history.

(56) References Cited

U.S. PATENT DOCUMENTS

| | | | | |
|---|---|---|---|---|
| 4,511,887 A | * | 4/1985 | Fiore | 340/539.16 |
| 4,945,367 A | * | 7/1990 | Blackshear | 396/427 |
| 5,742,233 A | * | 4/1998 | Hoffman et al. | 340/573.1 |
| 6,265,978 B1 | * | 7/2001 | Atlas | 340/575 |
| 6,825,767 B2 | * | 11/2004 | Humbard | 340/573.1 |
| 7,038,590 B2 | * | 5/2006 | Hoffman et al. | 340/573.1 |
| 2008/0045806 A1 | * | 2/2008 | Keppler | 600/300 |
| 2008/0076971 A1 | * | 3/2008 | Clapp | 600/300 |

* cited by examiner

*Primary Examiner* — Jennifer Mehmood
*Assistant Examiner* — Pameshanand Mahase
(74) *Attorney, Agent, or Firm* — Fay Sharpe LLP

(57) ABSTRACT

A security system is provided for a facility (10). The security system includes: a central monitoring station (20) that controls one or more security measures for the facility (10); and, a heart rate monitor (30) that detects a heart rate of an individual (50), the heart rate monitor (30) being in wireless communication with the central monitoring station (20). Suitably, the central monitoring station (20) selectively implements one or more of the security measures in response to a determination that an abnormal heart rate has been detected.

25 Claims, 2 Drawing Sheets

SECURITY SYSTEM TRIGGERED BY HEART RATE DETECTION

The present inventive subject matter relates to the art of security systems. Particular application is found in conjunction with certain types of security systems, and the specification makes particular reference thereto. However, it is to be appreciated that aspects of the present inventive subject matter are also amenable to other like applications and/or systems.

BACKGROUND

As is known in the art, banks and other businesses or enterprises employ security systems in their facilities to protect against robbery and/or theft, as well as, other types of unwanted activity that may be perpetrated by patrons or other like individuals and/or the enterprise's own employees or personnel. Commonly, a security system may include one or more security cameras that monitor the facility being protected. As can be appreciated, one function of a security camera is to obtain an image or video of a perpetrator so that they may be identified therefrom. For example, the image or video may later prove useful in apprehending the perpetrator and/or as evidence when prosecuting the perpetrator. Of course, a security camera may also serve as a deterrent, insomuch as a potential perpetrator may be less likely to commit a robbery, theft or otherwise unwanted activity if they know that they might get caught in the act by the camera. Additionally, a security system may include an alarm that signals for and/or summons aid when the alarm is tripped or triggered. As can be appreciated, summoning aid at the time that a robbery or theft or other unwanted activity is currently underway can have significant advantages, e.g., timely summoned law enforcement personnel may be able to foil a perpetrator's plans altogether. Nevertheless, various implementations of the foregoing security features have certain drawbacks.

For example, security cameras are often fixed in place and/or cover a substantially constant field of view (FOV). Accordingly, a perpetrator can thwart the security system by avoiding the camera's FOV. Optionally, a camera may be configured to automatically pan back and forth or otherwise scan a selected region. However, the cyclical nature of the camera movements produced by the automated control can allow a clever perpetrator to predict the direction in which the camera will be pointed at any given time, and accordingly, the perpetrator may still be able to avoid the camera's FOV. In both the foregoing examples, the direction in which the camera is pointed is not responsive to any information or data that indicates where in a facility a perpetrator may be located or where the otherwise unwanted activity is taking place.

In another example, a remote control camera optionally may be manually operated by a security guard or other individual. Accordingly, the human operator may select or control the direction in which the camera is pointed to observe and/or record a particular region of interest. This option however has the drawback that a human operator is needed to manually control the movement of the camera.

As previously indicated, security systems are also commonly equipped with alarms that may be selectively triggered to signal for and/or summon aid when circumstances dictate, e.g., when a robbery or other unwanted activity is in progress. In a common implementation, however, the alarm has to be triggered manually, e.g., by a bank teller, cashier or other employee at the facility being protected by the security system. For example, the individual responsible for setting off the alarm may be required to push a button, turn a key, flip a switch or otherwise manually trigger the alarm at the appropriate time.

A manually triggered alarm has certain drawbacks. Notably, the individual having the responsibility for triggering the alarm may not do so for any one or more of a variety of reasons. For example, in the case of a robbery or other emergency situation, the individual may panic and forget to trigger the alarm or forget how to trigger the alarm. Alternately, a perpetrator may threaten an individual so that they are too frightened for their own safety to trigger the alarm or the perpetrator may physically block or otherwise prevent the individual from triggering the alarm. In the case of employee theft, the very employee which would be otherwise responsible for triggering the alarm may in fact be the perpetrator of the unwanted activity and accordingly choose not to trigger the alarm. Similarly, an individual responsible for triggering the alarm (e.g., a bank teller or cashier) may be colluding with the perpetrator to commit the robbery, and accordingly the individual chooses not to trigger the alarm. As can be appreciated from the foregoing examples, there are any number of reasons why an individual otherwise responsible for triggering a manual alarm may choose not to or otherwise be prevented from doing so.

Accordingly, a new and improved security system and/or method is disclosed that overcomes the above-referenced problems and others.

SUMMARY

In accordance with one embodiment, a security system is provided for a facility. The security system includes: a central monitoring station that controls one or more security measures for the facility; and, a heart rate monitor that detects a heart rate of an individual, the heart rate monitor being in wireless communication with the central monitoring station. Suitably, the central monitoring station selectively implements one or more of the security measures in response to a determination that an abnormal heart rate has been detected.

In accordance with another embodiment, a method for controlling a security system is provided. The method includes: detecting a heart rate of an individual; determining if the detected heart rate is abnormal; generating a signal when it is determined that the detected heart rate is abnormal; wirelessly transmitting the generated signal; receiving the transmitted signal; and, selectively implementing one or more of security measures in response to the received the signal.

Numerous advantages and benefits of the inventive subject matter disclosed herein will become apparent to those of ordinary skill in the art upon reading and understanding the present specification.

BRIEF DESCRIPTION OF THE DRAWINGS

The inventive subject matter may take form in various components and arrangements of components, and in various steps and arrangements of steps. The drawings are only for purposes of illustrating preferred embodiments and are not to be construed as limiting. Further, it is to be appreciated that the drawings are not to scale.

DETAILED DESCRIPTION OF PREFERRED EMBODIMENTS

Figure 1:
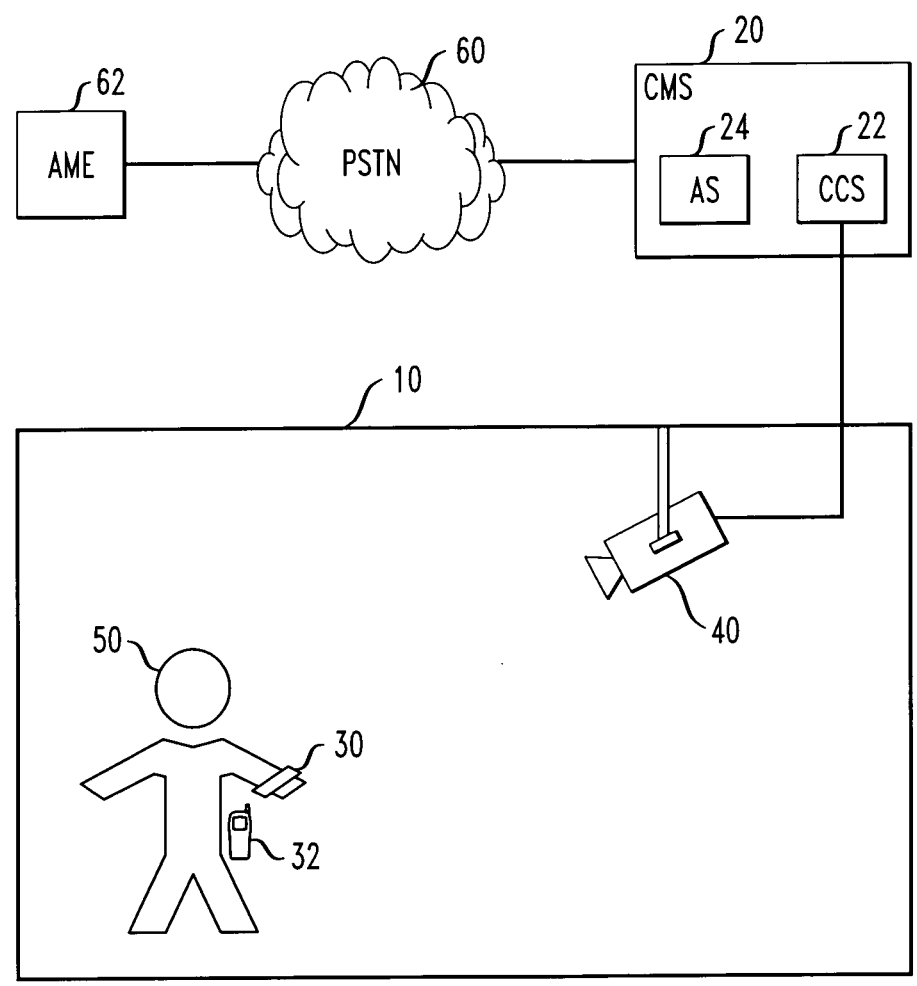
FIG. 1 is a block diagram illustrating an exemplary security system suitable for practicing aspects of the present inventive subject matter.

For clarity and simplicity, the present specification shall refer to structural and/or functional elements, entities and/or facilities, relevant communication standards, protocols and/or services, and other components that are commonly known in the art without further detailed explanation as to their configuration or operation except to the extent they have been modified or altered in accordance with and/or to accommodate the preferred embodiment(s) presented herein.

Ordinary individuals in various situations experience emotional and/or physical stress. For example, when being robbed or perceiving the threat of harm or danger or being exposed to other exigent circumstances, an individual often tends to experience fear or panic or other similar stress. Similarly, individuals engaged in certain activities also experience stress. For example, when engaged in dishonest activities such as theft or other prohibited activities, the perpetrator may also experience stress, such as the fear of getting caught or the exhilaration of engaging in illicit activities. Ordinary individuals experiencing fear or panic, exhilaration or other emotionally and/or physically stressful conditions typically exhibit certain biological changes or reactions that are essentially automatic or otherwise largely uncontrollable. One such biological reaction is a change in one's heart rate. For example, as the result of being exposed to a perceived threat of harm or danger or other exigent circumstances or as the result of engaging in certain illicit activities, an ordinary individual commonly experiences the fear, panic, exhilaration, etc. associated therewith, and in turn, the heart rate of the individual experiencing this stress tends to be elevated as compare to when the stress is not being experienced. In this way, an individual's heart rate is indicative of what they are experiencing and/or the activity in which they are engaged.

Accordingly, the present specification is generally directed to a security system and/or method in which the operation of selected security features are triggered and/or controlled in response to the heart rate of one or more individuals fitted with heart rate monitoring devices. A device worn by or otherwise fitted to an individual detects and/or otherwise monitors the heart rate of the wearer. Suitably, if the monitored heart rate varies for a determined period of time beyond a determined threshold from a baseline or normal heart rate for the individual fitted with the monitor, then one or more selected security features are triggered and/or controlled in response thereto. For example, when an abnormal heart rate is detected the monitor generates an appropriate signal or message indicative of the same. Optionally, as a result of the device signaling the detection of an abnormal heart rate, an alarm may be triggered and/or notification may be provided to a suitable authority or other entity to dispatch aid or a security camera may be trained or pointed in the appropriate direction and/or other security measures may be instituted.

More specifically, with reference to FIG. 1, there is shown a facility 10, e.g., which may be operated as and/or by a bank, business or other enterprise that is protected by a security system. Optionally, the facility 10 may also represent a home or residence. As shown, the security system includes a central monitoring station (CMS) 20, a heart rate monitor 30, and optionally a security camera 40 (e.g., which may be a still image camera or video camera). Also shown in FIG. 1 is an individual 50, e.g., which may be an employee or other like individual located in and/or about the facility 10. Suitably, the individual 50 may be, for example, a bank teller, convenience store cashier, home owner or other resident of the facility 10, etc.

For purposes of simplicity and clarity herein, only one individual, one monitor and one camera have been shown in FIG. 1. However, it is to be appreciated, that the security system may optionally be equipped with a plurality of similar monitors to monitor a plurality of similarly situated individuals. Likewise, the security system may optionally be equipped with a plurality of similar cameras to provide coverage of one or more regions or locations in and/or about the facility 10. Additionally, while the CMS 20 is shown serving only one facility, it is to be appreciated, that in practice, one CMS may optionally serve a plurality of facilities.

As shown in FIG. 1, the CMS 20 includes a camera control subsystem (CCS) 22 which is operatively connected to the camera 40 and an alarm subsystem (AS) 24. The CCS 22 controls the operation of the camera 40 at the direction of the CMS 20, and the AS 24 controls an alarm function which is triggered at the direction of the CMS 20. Suitably, the monitor 30 is in operative communication with the CMS 20 via an appropriate wireless connection or channel. For example, the monitor 30 optionally communicates with the CMS 20 via a wireless local area network (WLAN) connection or other suitable wireless interface. In an alternate embodiment, the monitor 30 may be a Bluetooth or similarly enabled device in operative communication with a Bluetooth or similarly enabled mobile station (MS) 32 (e.g., a cellular or mobile telephone) carried by the individual 50 and/or otherwise employed to operatively communicate information and/or data from the monitor 30 and/or MS 32 over a public cellular or wireless telecommunications network to a remotely located CMS 20.

In the illustrated embodiment, the AS 24 is operatively connected in the usual manner to a suitable telecommunications network, e.g., the public switched telephone network (PSTN) 60. Additionally, an alarm monitoring entity (AME) 62 is likewise operatively connected to the PSTN 60 in the usual manner. For example, the AME 62 may optionally be a monitoring service that in turn notifies the appropriate authorities (e.g., a suitable law enforcement agency) when it receives an alarm from the AS 24, or alternately, the AME 62 optionally represents the appropriate authority itself. In yet another example, the AME 62 may be a PSAP (Public Safety Answering Point). In any case, suitably, when the alarm function is triggered (e.g., due to the detection of an abnormal heart rate), the AS 24 optionally establishes a connection over the PSTN 60 with the AME 62 to communicate or otherwise notify the AME 62 of the alarm condition so that aid may be dispatched as deemed appropriate. Alternately, a dedicated connection is provided between the AS 24 and the AME 62. In yet another embodiment, the CMS 20 may in fact reside at or otherwise be coextensive with the AME 62.

Suitably, the monitor 30 is worn by or otherwise fitted to the individual 50 and detects and/or otherwise monitors the heart rate of the wearer. For example, suitable heart rate monitors are known which are worn across the chest or about the wrist of the user. Optionally, the chest strap type of monitor may be concealed under appropriate clothing. However, it is to be appreciated, that any suitable type of heart rate monitor may be employed for the purpose of detecting the wear's heart rate.

In operation, if the monitored heart rate of the individual 50 varies from a baseline or normal heart rate for the individual 50 fitted with the monitor 30, then an abnormal heart rate signal or message is generated. Optionally, the monitored heart rate is only deemed abnormal when the monitored heart rate varies beyond a determined threshold from the baseline or normal heart rate for a determined period of time. In this way, false abnormal heart rate signals which would otherwise be generated by momentary and/or insignificant variations in the wearer's heart rate are avoided. Suitably, the abnormal heart rate determination is made by the monitor 30 and an appropriate signal or message is sent wirelessly to the CMS 20. Alternately, heart rate data is collected by the monitor 30 and sent wirelessly to the CMS 20 which in turn analyzes the data to determine if an abnormal heart rate exists.

Suitably, the CMS 20 also obtains position data or information indicating the location of the individual 50 wearing or otherwise fitted with the monitor 30. In one suitable embodiment, the established location of the individual 50 is optionally used by the CMS 20 to direct the operation of the camera 40. For example, the position data or information obtained by the CMS 20 is provided to the CCS 22 which in turn optionally controls the movement and/or operation of the camera 40 in response to the received position data or information so that the camera 40 is trained on and/or pointed in the direction of the established location within the facility 10. In another suitable embodiment, the established location of the individual 50 is also communicated via the AS 24 to the AME 62 so that aid can be dispatched to the appropriate facility 10 and/or specific location within the facility 10. In any event, the location of the individual 50 is optionally established in one or more of a variety of manners.

In one suitable embodiment, the CMS 20 obtains a unique identifier (ID) which is associated with the monitor 30 and/or the monitor's wearer 50. For example, the ID may be transmitted by the monitor 30 along with the heart rate data and/or the abnormal heart rate signal or message sent to the CMS 20. Alternately, the ID may be a telephone number or MIN (Mobile Identification Number) or other like ID associated with the MS 32 used to forward the heart rate data and/or abnormal heart rate signal or message sent to the CMS 20. In either case, suitably, the CMS 20 is provisioned with a location database (DB) or table or the like that relates various IDs to specific locations. Accordingly, the obtained ID is optionally employed by the CMS 20 to reference the corresponding location in the location DB or table. In this manner, a location of the monitor 30 and/or individual 50 is established. Such an approach is useful, e.g., when a particular monitor 30 and/or wearer 50 is closely tied to a particular location. For example, in a bank, a particular monitor 30 may be designated for a teller or wearer 50 that is assigned to a specific teller window. Accordingly, the location of the specific teller window is associated with the respective ID in the aforementioned DB or table. Therefore, when an abnormal heart rate is detected that corresponds to an obtained ID associated with the monitor 30 or wearer 50 assigned to the specific teller window, the CMS 20 establishes the location of the monitor 30 and/or wear 50 by using the obtained ID to look-up the specific location of the teller window in the location DB or table that is associated with the matching ID. As can be appreciated, however, this approach is not well suited to situations where a particular monitor 30 and/or wearer 50 is not closely tied to a particular location.

Accordingly, in another suitable embodiment, the monitor 30 and/or MS 32 is optionally equipped or otherwise provisioned with a GPS (Global Positioning System) receiver or other like autonomous or self-aware geo-spatial positioning device capable of determining its own position. Suitably, along with the heart rate data or abnormal heart rate signal or message sent or otherwise provided to the CMS 20, the monitor 30 and/or MS 32 also sends or otherwise provides the CMS 20 with position data or information corresponding to the current location of the monitor 30 and/or MS 32, e.g., generated by and/or otherwise obtained via the GPS receiver or other like device. In this manner, the location of the individual 50 wearing or otherwise fitted with the monitor 30 and/or carrying the MS 32 is made available to the CMS 20. Consequently, the actual location of the individual 50 can be accurately established even if they are not closely tied to a particular location.

Figure 2:
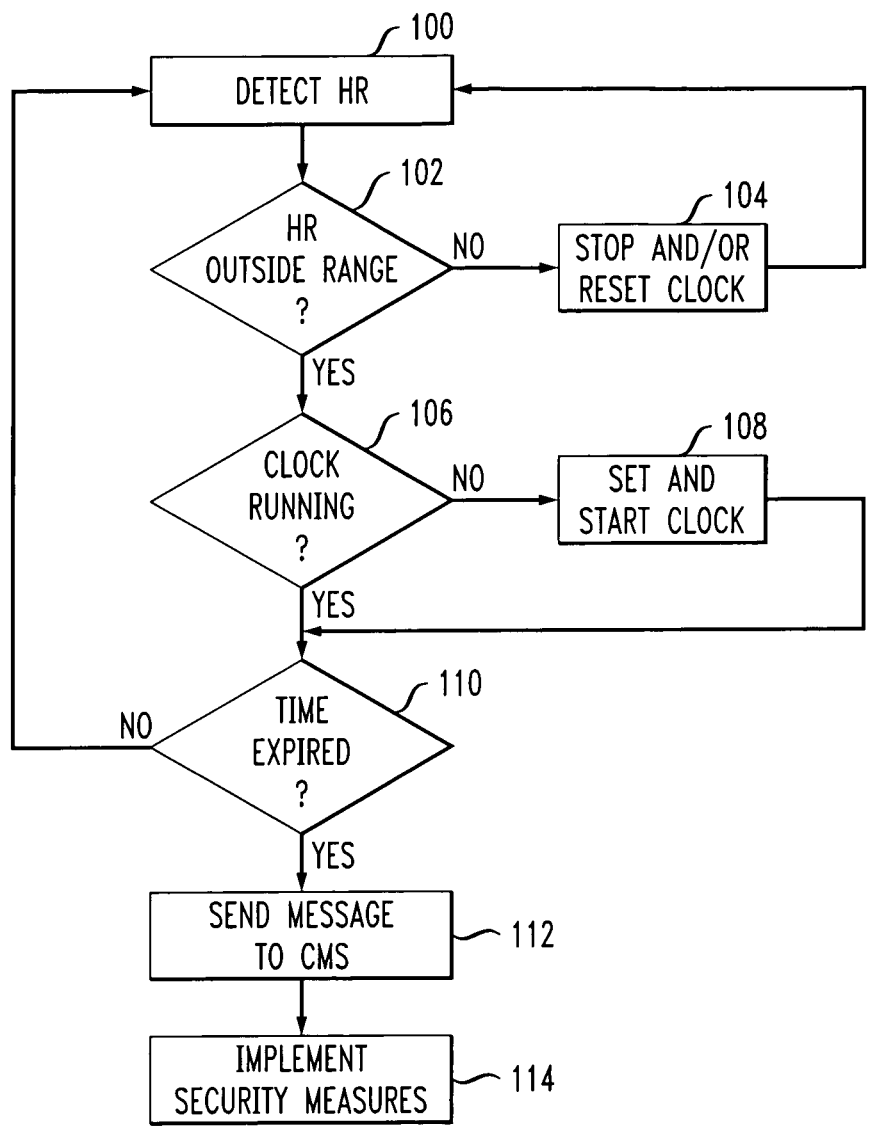
FIG. 2 is a flow chart showing an exemplary process embodying aspects of the present inventive subject matter.

With reference to FIG. 2, there is shown an exemplary process by which an abnormal heart rate of the individual 50 is detected and used to trigger the implementation of selected security measures.

At step 100, the monitor 30 worn by and/or otherwise fitted to the individual 50 detects the heart rate (HR) of the individual.

At decision step 102, the monitor 30 determines if the detected HR is outside a normal or acceptable range for the individual 50. Suitably, for example, the monitor 30 is programmed or otherwise provisioned with a baseline or normal HR for the individual 50 and the acceptable range is defined about the baseline HR. Optionally, threshold limits (e.g., as a selected percentage of variance) above and/or below the baseline are set or otherwise determined to define the acceptable range. If the detected HR is not outside the acceptable range, then the process branches to step 104 where an internal clock or timer is stopped and/or reset, and eventually from step 104 the process loops back to step 100. Alternately, if the detected HR is outside the acceptable range, then the process continues to step 104.

At decision step 104, the monitor 30 checks its internal clock or timer to determine whether or not the clock or timer is already running. As can be appreciated, if the previously detected HR was not outside the acceptable range, then the clock or timer should not already be running insomuch as at step 104 it would have been stopped and/or reset. If at step 104 it is determined that the clock or timer is not already running, then the process branches to step 108 where the clock or timer is set and/or started, and from step 108 the process continues to step 110. Suitably, the clock or timer is set to lapse or expire after a sufficient period of time so that transitory variations in the detected HR do not result in false positives. If at step 104 it is determined that the clock or timer is already running, similarly the process continues to step 110, albeit in this case bypassing step 108.

At decision step 110, the monitor 30 determines if the time has expired, e.g., by checking its internal clock or timer. If the time has not expired, then the process loops back to step 100, otherwise the process continues on to step 112. As can be appreciated, reaching step 112 means that the monitor 30 has detected an abnormal HR, i.e., a HR which remains outside the defined normal or acceptable range for a period of time defined by the monitor's internal clock or timer.

At step 112, the monitor 30 generates and wirelessly sends a signal or message to the CMS 20 indicating that the abnormal HR has been detected. Optionally, the signal or message also includes the monitor's ID and/or position data or information, e.g., obtained from the GPS received or other like device provisioned in the monitor 30. Suitably, when the CMS 20 is located in or near the facility 10, a WLAN connection or other similar wireless connection or channel may be used to transmit the signal or message. In another optional embodiment (e.g., where the CMS 20 is remotely located with respect to the facility 10), the monitor 30 may merely signal or instruct the MS 32, e.g., via a Bluetooth or other similar connection, to transmit the appropriate signal or message to the CMS 20. For example, upon receiving the signal that indicates that the monitor 30 has detected an abnormal HR, the MS 32 is optionally programmed and/or otherwise provisioned to automatically place a call over the serving cellular or wireless telecommunications network to a designated telephone number or address, thereby establishing a connection with the CMS 20. Accordingly, via this connection, the signal or message is relayed to the CMS 20. Alternately, the MS 32 is optionally programmed and/or otherwise provisioned to generate and/or send the signal and/or other relevant information and/or data in an instant message, SMS (Short Message Service) message or other like text message.

Suitably, when the MS 32 is utilized to transmit the abnormal HR signal or message to the CMS 20, the MS 32 optionally also includes the position data or information, e.g., obtained from the GPS receiver or other like device provisioned in the MS 32. Additionally, the CMS 20 optionally obtains the MIN or other similar ID associated with the MS 32 to identify the individual 50 to which the signal or message pertains. Accordingly, the monitor 30 is relieved of these burdens and the corresponding equipment may optionally be omitted. Moreover, being that it is common for a typical MS to already be provisioned with GPS capabilities, this approach realizes the added benefit of utilizing equipment and/or capabilities already available.

At step 114, having received the abnormal HR signal or message, the CMS 20 implements selected security measures. For example, under the direction of the CMS 20, the AS 24 optionally triggers the alarm function. Suitably, when the alarm function is triggered, the AS 24 establishes a connection over the PSTN 60 with the AME 62 thereby alerting the AME 62 that the alarm has been triggered so that the AME 62 may arrange to dispatch suitable aid as may be deemed appropriate, for example law enforcement personnel. Optionally, the CMS 20 provides the AS 24 with the established location, e.g., based upon the received position data or information obtained from the monitor 30 or MS 32. Accordingly, the AS 24 in turn provides the established location to the AME 62 so that aid can be dispatched to the proper facility 10 or the specific location within the facility 10. Moreover, the CMS 20 also optionally provides the received position data or information obtained from the monitor 30 or MS 32 to the CCS 22. In response thereto, the CCS 22 controls the operation and/or movement of the camera 40, e.g., so that the camera 40 is trained on and/or pointed in the direction of the established location within the facility 10.

As described herein, the security system is responsive and/or reactive to the heart rate of the individual 50. Accordingly, if the individual 50 is exposed to a stressful situation (e.g., such as a robbery) or is engaged in illicit activities (e.g., such as committing theft), then the associated fear, panic, exhilaration, etc. will typically be accompanied by an increased heart rate that will be detected by the monitor 30 and result in the selected security measures being automatically implemented. Additionally, a significant drop in heart rate is also optionally detected by the monitor 30 and may likewise result in selected security measures being automatically implemented. For example, if the monitor 30 detects no heart rate or some other sufficiently low heart rate, this could indicate that the wearer 50 was seriously injured or kill, e.g., as the result of an attempted robbery. Alternately, detecting no heart rate may indicate that the wearer 50 intentionally removed the monitor 30 in an attempt to defeat the security system, e.g., as a prelude to engaging in illicit activity. Suitably, the selected security measures implemented in any given instance are accordingly dependent upon whether an increased HR is detected or a decreased HR is detected.

It is to be appreciated that in connection with the particular exemplary embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof.

What is claimed is:

1. A security system for a facility, said security system comprising:
    a central monitoring station that controls one or more security measures for protection of the facility; and,
    a heart rate monitor disposed in relation to an individual expected to be situated in or about the facility that detects a heart rate of the individual, said heart rate monitor being in wireless communication with the central monitoring station;
    wherein the central monitoring station selectively implements one or more of the security measures for protection of the facility in response to a determination that the heart rate detected by the heart rate monitor is abnormal and elevated above a normal heart rate for the individual, the elevated heart rate being indicative of the individual experiencing stress due to exposure to an unwanted activity at the facility.

2. The system of claim 1, wherein the determination that the monitored heart rate is abnormal is made when the detected heart rate varies for a determined period of time beyond a determined threshold from a baseline heart rate for the individual.

3. The system of claim 1, further comprising:
    means for obtaining an established location of at least one of the heart rate monitor and the individual, wherein the established location is used by the central monitoring station in selectively implementing the one or more security measures.

4. The system of claim 1, further comprising:
    an alarm subsystem controlled by the central monitoring station, said alarm subsystem triggering an alarm condition and notifying an alarm monitoring entity of the alarm condition in conjunction with implementation of the one or more security measures by the central monitoring station.

5. The system of claim 3, further comprising:
a camera control subsystem controlled by the central monitoring station, said camera control subsystem operating and pointing a security camera arranged in or about the facility to the established location in conjunction with implementation of the one or more security measures by the central monitoring station.

6. The system of claim 3, wherein the means for obtaining an established location comprises a geo-spatial positioning device disposed in relation to at least one of the heart rate monitor and the individual and in operative communication with the central monitoring station to provide the central monitoring station with position information, wherein the established location obtained by the central monitoring station is based at least in part on the position information.

7. The system of claim 1, further comprising:
a mobile station disposed in relation to at least one of the heart rate monitor and the individual and served by a wireless telecommunications network, said mobile station being in operative communication with the heart rate monitor via a wireless link, wherein wireless communication between the heart rate monitor and the central monitoring station is via the mobile station.

8. A method for controlling a security system for a facility, said method comprising:
(a) detecting a heart rate of an individual expected to be situated in or about the facility using a heart rate monitor disposed in relation to the individual;
(b) determining the detected heart rate is abnormal and elevated above a normal heart rate for the individual, the elevated heart rate being indicative of the individual experiencing stress due to exposure to an unwanted activity at the facility; and,
(c) selectively implementing one or more security measures for protection of the facility in response to the determining in (b).

9. The method of claim 8, further comprising:
deeming the heart rate of the individual is abnormal when the detected heart rate remains beyond a determined threshold from a baseline heart rate for the individual for a determined period of time.

10. The method of claim 8, further comprising:
obtaining an established location of at least one of the heart rate monitor and the individual; and
using the established location in selectively implementing the one or more security measures.

11. The method of claim 10, further comprising:
receiving position information from a geo-spatial positioning device disposed in relation to at least one of the heart rate monitor and the individual, wherein the established location is based at least in part on the position information.

12. The method of claim 8, further comprising:
triggering an alarm condition in conjunction with implementation of the one or more security measures; and
notifying an alarm monitoring entity of the alarm condition.

13. The method of claim 12, further comprising:
obtaining an established location of at least one of the heart rate monitor and the individual; and
communicating the established location to the alarm monitoring entity.

14. The method of claim 10, further comprising:
controlling operation of a security camera arranged in or about the facility; and
pointing the security camera to the established location in conjunction with implementation of the one or more security measures.

15. The system of claim 2 wherein the central monitoring station makes the abnormal heart rate determination based on heart rate data received from the heart rate monitor.

16. The system of claim 2 wherein the heart rate monitor makes the abnormal heart rate determination, generates an abnormal heart rate signal or message indicative of the abnormal heart rate determination, and sends the abnormal heart rate signal or message to the central monitoring station.

17. The system of claim 3, the means for obtaining an established location comprising:
a location database storing location information for a plurality of locations, the plurality of locations corresponding to specific locations in or about the facility in which a corresponding plurality of individuals are expected to be situated; and
means for obtaining a unique identifier associated with the individual, the unique identifier relating to location information for a specific location in the location database in which the individual is expected to be situated;
wherein the location database and means for obtaining a unique identifier are used by the central monitoring station such that the established location obtained by the central monitoring station is based at least in part on the specific location in the location database in which the individual is expected to be situated.

18. The method of claim 8, further comprising:
receiving heart rate data from the heart rate monitor;
wherein the abnormal heart rate determination is based at least in part on the heart rate data.

19. The method of claim 8, further comprising:
receiving an abnormal heart rate signal or message indicative of the abnormal heart rate determination from the heart rate monitor after the heart rate monitor makes the abnormal heart rate determination.

20. The method of claim 19, further comprising:
receiving the abnormal heart rate signal or message from a mobile station via a wireless telecommunications network, the mobile station disposed in relation to at least one of the heart rate monitor and the individual, the mobile station being in operative communication with the heart rate monitor via a wireless link.

21. The method of claim 10, further comprising:
storing a plurality of locations in a locations database, the plurality of locations corresponding to specific locations in or about the facility in which a corresponding plurality of individuals are expected to be situated; and
obtaining a unique identifier associated with the individual, the unique identifier relating to location information for a specific location in the location database in which the individual is expected to be situated;
wherein the established location obtained is based at least in part on the specific location in the location database in which the individual is expected to be situated.

22. A method of protecting a facility from unwanted activity, comprising:
a) receiving an abnormal heart rate signal or message indicating that a heart rate of an individual expected to be situated in or about the facility is abnormal, the heart rate of the individual being detected by a heart rate monitor disposed in relation to the individual, the abnormal heart rate determination being made by the heart rate monitor, wherein the abnormal heart rate determination for the individual is based on the detected heart rate being beyond a determined threshold from a baseline heart rate for the individual for a determined period of time, the detected heart rate being elevated above the baseline heart rate, the elevated heart rate being indicative of the individual experiencing stress due to exposure to an unwanted activity at the facility;
b) obtaining an established location of at least one of the heart rate monitor and the individual;
c) selectively implementing one or more security measures for protection of the facility in response to receiving the abnormal heart rate signal or message and using the established location;
d) controlling operation of a security camera arranged in or about the facility and pointing the security camera to the established location in conjunction with implementation of the one or more security measures; and
e) triggering an alarm condition in conjunction with implementation of the one or more security measures and notifying an alarm monitoring entity of the alarm condition.

23. The method of claim 22, further comprising:
f) storing a plurality of locations in a locations database, the plurality of locations corresponding to specific locations in or about the facility in which a corresponding plurality of individuals are expected to be situated; and
g) obtaining a unique identifier associated with the individual, the unique identifier relating to location information for a specific location in the location database in which the individual is expected to be situated;
wherein the established location obtained is based at least in part on the specific location in the location database in which the individual is expected to be situated.

24. The method of claim 23, further comprising:
h) receiving the unique identifier from a mobile station via a wireless telecommunications network, the mobile station disposed in relation to at least one of the heart rate monitor and the individual, the mobile station being in operative communication with the heart rate monitor via a wireless link.

25. The method of claim 22, further comprising:
f) receiving the abnormal heart rate signal or message from a mobile station via a wireless telecommunications network, the mobile station disposed in relation to at least one of the heart rate monitor and the individual, the mobile station being in operative communication with the heart rate monitor via a wireless link.

* * * * *